United States Patent [19]
Morejohn et al.

[11] Patent Number: 6,146,394
[45] Date of Patent: Nov. 14, 2000

[54] VASCULAR CLAMP AND METHOD FOR USING THE SAME

[75] Inventors: Dwight P. Morejohn, Davis; Ivan Septeka, Los Altos; Robert C. Glines, Cameron Park, all of Calif.

[73] Assignee: Cardiothoracic Systems, Inc., Cupertino, Calif.

[21] Appl. No.: 09/472,651

[22] Filed: Dec. 27, 1999

Related U.S. Application Data

[62] Division of application No. 09/042,307, Mar. 13, 1998, Pat. No. 6,036,706.

[51] Int. Cl.7 .................................................. A61B 17/04
[52] U.S. Cl. ............................................ 606/158; 606/157
[58] Field of Search .................................. 606/139, 157, 606/151, 158, 201

[56] References Cited

U.S. PATENT DOCUMENTS

| | | | |
|---|---|---|---|
| 5,236,437 | 8/1993 | Wilk et al. | 606/207 |
| 5,464,421 | 11/1995 | Wortrich | 606/213 |
| 5,618,307 | 4/1997 | Donlon et al. | 606/205 |
| 5,624,454 | 4/1997 | Palti et al. | 606/151 |
| 5,683,405 | 11/1997 | Yacoubian et al. | 606/158 |
| 5,697,942 | 12/1997 | Palti | 606/151 |

*Primary Examiner*—Gary Jackson
*Attorney, Agent, or Firm*—Fenwick & West, LLP

[57] ABSTRACT

The present invention relates to a vascular clamp assembly. The vascular clamp assembly includes at least one bendable elongated shaft with a proximal part and distal part. A pair of clamping members are located at the distal part of the shaft. The clamp includes means for moving the clamping members between an open position and a clamping position.

14 Claims, 6 Drawing Sheets

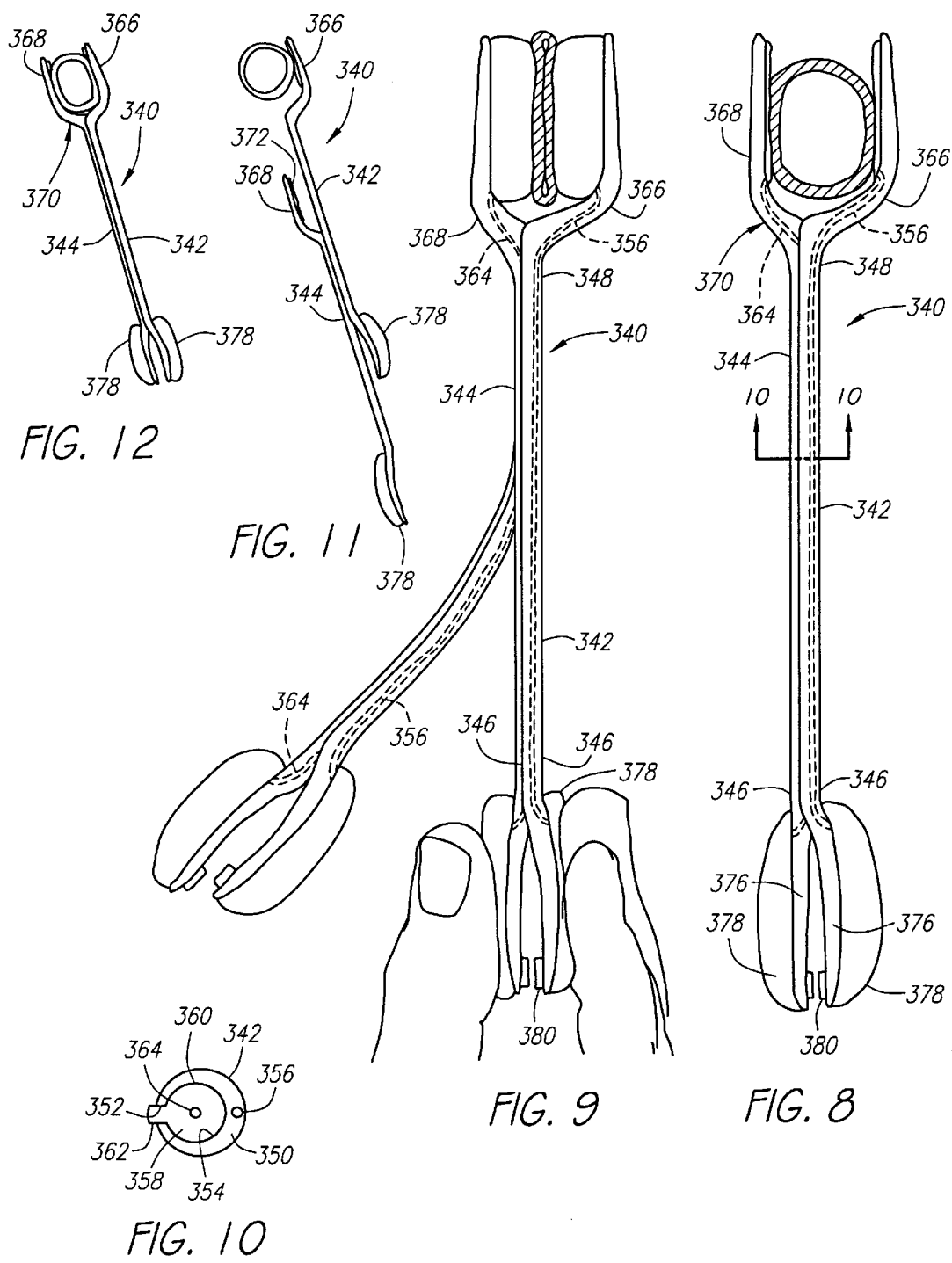

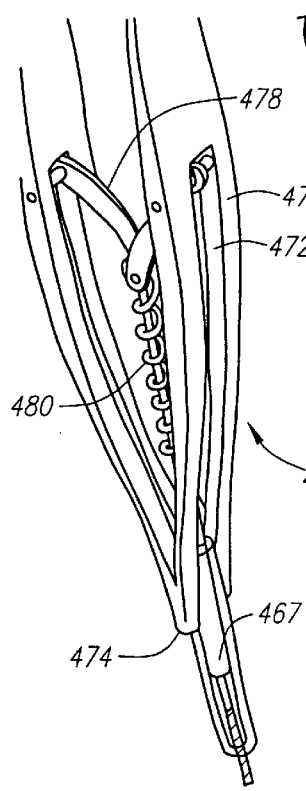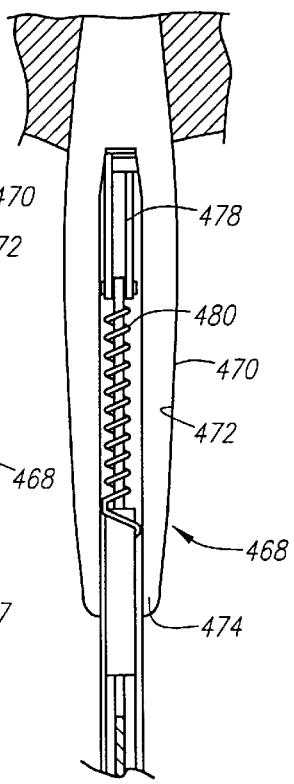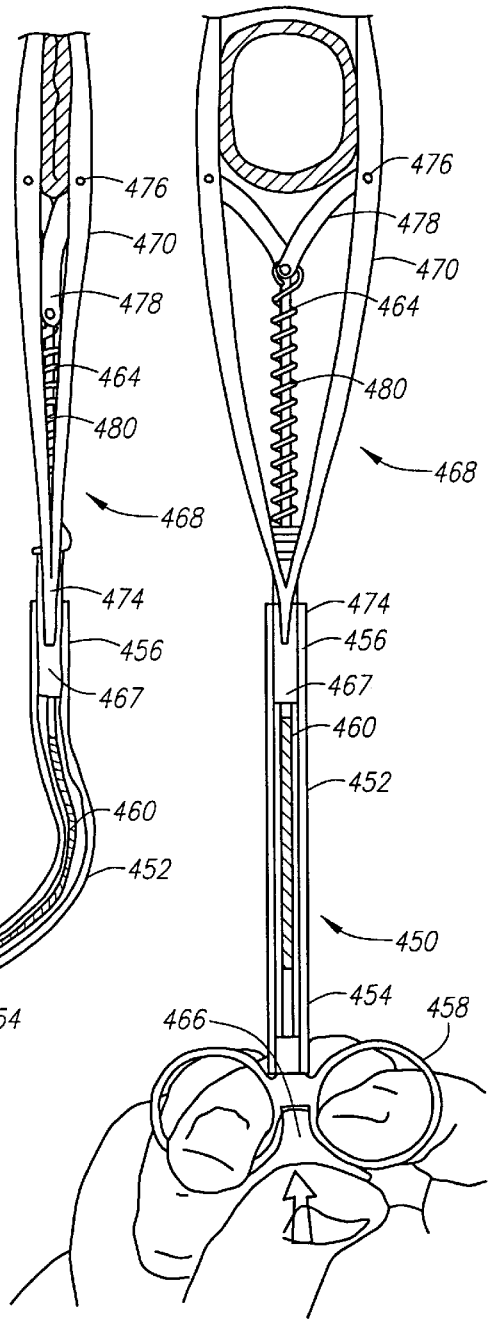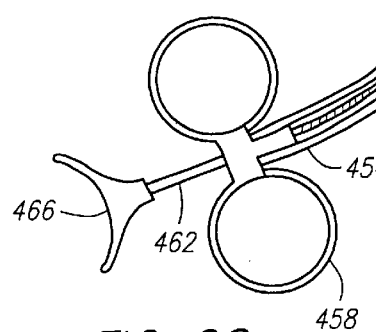

VASCULAR CLAMP AND METHOD FOR USING THE SAME

This is a divisional of application Ser. No. 09/042,307 filed on Mar. 13, 1998 now U.S. Pat. No. 6,036,706. The priority of this application is expressly claimed and disclosure is hereby incorporated by reference.

FIELD OF THE INVENTION

This invention relates generally to surgical instruments for temporarily occluding a blood vessel during surgical procedures, and more particularly to vascular clamps for temporarily occluding a blood vessel during cardiopulmonary bypass (CPB) to facilitate the performance of cardiac procedures.

BACKGROUND OF THE INVENTION

To facilitate the reader's understanding of the present invention, the CPB process is generally described below, followed by a description of the problems with vascular clamps used during the CPB process in the past.

The descriptive terms upstream and downstream, when used herein in relation to the patient's vasculature, refer to directions closer to and further from the heart in the arterial system, and the opposite in the venous system. The terms proximal and distal, when used herein in relation to instruments, refer to directions closer to and farther away from the operator of the instrument, respectively.

During CPB, it is desirable to provide life-support functions, a motionless, decompressed heart and a dry, bloodless field of view for the surgeon. In a basic CPB system, oxygen-poor blood is drained by means of gravity or is syphoned from the patient's venous circulation and is transported to a pump-oxygenator, commonly known as the heart-lung machine, where the blood is exposed to a gaseous mixture that eliminates carbon dioxide and adds oxygen to the blood. The oxygenated blood is then returned or perfused into the patient's arterial circulation for distribution throughout the entire body. This process requires a venous drainage cannula (or cannulae) to be placed into the right side of the heart (typically the right atrium) or directly in the major veins (typically the superior vena cava (SVC) and/or inferior vena cava (IVC)) or through peripheral vein access sites to drain unoxygenated blood from the patient and deliver it to the heart-lung machine. Similarly, an arterial or aortic perfusion cannula is placed in the aorta or another large peripheral artery, such as the common femoral artery, to return or perfuse oxygenated blood to the patient. The heart and lungs of the person can thereby be effectively bypassed, thus allowing the surgeon to operate on a bloodless heart.

The insertion of the arterial (aortic) perfusion cannula is usually performed in the following fashion. After an incision is made in the patient's chest and the pericardium (the protective sac around the heart) has been entered, two concentric purse string sutures are placed into the anterior wall of the ascending aorta just proximal to upstream of the brachiocephalic trunk. A "choker" tube or sleeve is positioned over the trailing ends of the suture threads to act as a tourniquet for tightening the purse string suture. A small incision is then made through the wall of the aorta into its lumen in the center of the purse-string sutures. The aortic perfusion cannula is then quickly inserted through that incision into the lumen of the aorta, taking care to minimize the escape of blood from the puncture site. The purse string sutures are then tightened by means of their respective tourniquets to seal the aortic wall around the perfusion cannula in order to prevent the escape of blood from the aorta. Air is then evacuated from the perfusion cannula as it is joined by a connector to the tubing from the pump-oxygenator. A mechanical cross-clamp, i.e., vascular clamp, is placed on the ascending aorta just downstream of the aortic root and upstream of the cannula to ensure that no blood flows back into the aorta during CPB.

The venous drainage cannula(e) is (are) inserted in a similar manner directly through an incision in the right atrium of the heart or into the superior and/or inferior vena cava for connection to the drainage side of the pump-oxygenator. Once the requisite cannulae are in place and the connections are made to the heart-lung machine, CPB is instituted by allowing unoxygenated blood returning to the right side of the heart to be diverted through the venous drainage cannula(e) and into the pump-oxygenator where it is oxygenated and temperature-adjusted. From there, the blood is pumped into the patient's arterial system via the arterial or aortic perfusion cannula to provide oxygen rich blood to the patient's body and brain.

After CPB has been established, the process known as cardioplegia, which literally means "heart stop," is used to arrest the beating of the heart, and in some procedures, to provide oxygen to the myocardium. Cardioplegia is administered by delivering a cardioplegic solution, such as potassium, magnesium, procaine, or a hypoclacemic solution, to the myocardium by antegrade and/or retrograde perfusion. For example, cardioplegia may be administered by inserting a needle into the aorta upstream of the aortic cross-clamp and injecting cardioplegic solution into the aortic root. The cardioplegic solution drains in the normal direction of blood flow into the coronary ostia, through the coronary arteries, and into the capillaries within the myocardium.

The problems with conventional vascular clamps used during the CPB process will now be described. As previously mentioned, the vascular cross-clamp is placed externally on the ascending aorta through an incision or opening in the chest. Traditionally, when cardiac procedures are to be performed, the sternum is cut longitudinally (a median sternotomy), providing access between opposing halves of the anterior portion of the rib cage to the heart and other thoracic vessels and organs. Alternatively, a lateral thoracotomy is formed, wherein a large incision is made between two ribs. A portion of one or more ribs may be permanently removed to optimize access. Either of these techniques provides a substantial opening in the chest, giving the surgeon a relatively large working area through which to operate.

A problem with these techniques for accessing the heart area is that they cause the patient significant trauma. The patient requires immediate postoperative care in an intensive care unit, a total period of hospitalization of up to seven to ten days, and a recovery period that can be as long as six to eight weeks.

In more modern, minimally invasive cardiac surgery, smaller incisions are made in the chest at various strategic locations. The surgical instruments are introduced at these locations. An endoscope is provided at one of these locations, and selected surgical instruments are manipulated by the surgeon with the aid of the endoscope. Accessing the heart area with minimally invasive techniques causes the patient less trauma than the techniques described previously.

A problem with all of the aforementioned techniques for accessing the heart area, especially minimally invasive techniques, is that the access area or the incision area is very limited in size. The larger and/or the greater the number of surgical instruments, the more they interfere with the cardiac procedures to be performed.

Vascular clamps in the past have traditionally had long and/or large shafts and handles that tend to obstruct the access area during cardiac surgery. Some vascular clamps in the past have included "bulldog" clamps, or similar clamps, to alleviate this problem. A "bulldog" clamp is a small V-shaped clamp that is applied to a blood vessel with an applier, such as forceps, and left on the blood vessel until it needs to be removed. Once the "bulldog" clamp is applied to the blood vessel, the applier is removed from the operating site, reducing the interfering effect the cross-clamp has on the surgical procedure. A problem with "bulldog" clamps and related clamps is that they do not give the operator immediate control over the opening and closing of the clamp. If the clamp needs to be opened, an instrument, usually different than the applier, must be delivered to the surgeon, introduced through the incision, and used to remove the clamp. This opening process takes too long if blood flow through the clamped blood vessel is immediately necessary.

A need therefore exists for a vascular clamp that does not take up a significant amount of space at the operating site, yet provides the operator with immediate control over the clamp.

A problem with vascular clamps that relates more to minimally invasive cardiac procedures is that they typically have a construction that makes them difficult to introduce through a narrow insertion in the chest, and, once in the chest, they are difficult to manipulate around body tissue to the blood vessel to be clamped.

An additional need therefore exists for a vascular clamp that has a construction that facilitates introduction through a narrow insertion in the chest, and manipulation around tissue within the body to the blood vessel to be clamped.

In the past, vascular clamps, once they were clamped to the blood vessel, are usually held in the closed position manually by the operator, or with a locking mechanism. Manually maintaining the clamp in the closed position is desirable in that it gives the operator a better feel for the pliability of the blood vessel; however, it also introduces the possibility of operator error. For example, too much pressure on the blood vessel will damage the blood vessel, and insufficient pressure will not preclude blood flow through the blood vessel. Particularly for clamps without attached handles, quick removal of the clamp is difficult if blood flow through the blood vessel becomes immediately necessary.

Therefore, a further need exists for a vascular clamp that includes a locking mechanism that allows for the immediate release of the clamp.

SUMMARY OF THE INVENTION

An additional aspect of the present invention involves a vascular clamp suitable for temporarily occluding a blood vessel during surgery. The vascular clamp includes at least one bendable -elongated shaft with a proximal part and distal part. A pair of clamping members are located at the distal part of the shaft. The clamp includes means for moving the clamping members apart from each other to an open position for surrounding a portion of the blood vessel and towards each other to a clamping position for compressing the blood vessel with pressure sufficient to occlude blood flow through the blood vessel. After the clamp is applied to the blood vessel, the elongated shaft is bent away from the surgical area of interest, reducing the obstructing effect of the vascular clamp on the surgery.

The vascular clamp assembly includes a locking or maintaining means adapted to maintain the clamping members in the clamping position and may include a quick release mechanism adapted to disengage the locking or maintaining means upon actuation of the quick release mechanism, allowing immediate movement of the clamping members.

The at least one bendable elongated shaft may include a pair of elongated shafts that are slidable lengthwise relative to each and rotatable relative to each other. This construction allows one half of the vascular clamp to be applied to the blood vessel at a time. The ability to apply one half of the vascular clamp at a time facilitates introduction of the vascular clamp through a narrow insertion site, and manipulation around tissue within the body to the blood vessel to be clamped.

A further aspect of the invention involves a method of temporarily occluding a blood vessel during surgery. The method includes a number of steps, one of which is providing a vascular clamp with at least one bendable elongated shaft having a proximal part and distal part. A pair of clamping members are located at the distal part of the shaft. The vascular clamp includes means for moving the clamping members apart from each other to an open position and towards each other to a clamping position. The method also includes the steps of clamping the blood vessel by compressing the blood vessel with the clamping members with pressure sufficient to occlude body flow through the section, and bending the elongated shaft away from the surgical area of the interest so that the obstructing effect of the vascular clamp on the surgery is reduced.

BRIEF DESCRIPTION OF THE DRAWINGS

These and other features of the invention will now be described with reference to the drawings of the embodiment, which are intended to illustrate and are not to limit the invention, and in which:

FIG. 8 is a top view of an additional embodiment of the vascular clamp of the present invention, and shows the clamp partially surrounding a vessel;

FIG. 9 is a top view of the vascular clamp of FIG. 8, and shows the clamp applied to a vessel and the handle in a bent-away position, as well as showing its proximal inflation device being manually pumped;

FIG. 10 is a cross-sectional view of the vascular clamp handle of FIG. 8 taken along lines 16—16 of FIG. 8;

FIGS. 11 and 12 are top views of the vascular clamp of FIG. 8, and show the clamp being applied to a vessel;

FIG. 18 is a top view of an additional embodiment of the vascular clamp of the present invention, and shows the clamping members in an open position, partially surrounding a vessel;

FIG. 19 is partial, perspective view of the distal portion of the vascular clamp of FIG. 28, and shows the clamping members in an open position;

FIG. 20 is a top view, similar to FIG. 28, and shows the shaft and handle in a bent-away position and the clamp applied to a vessel; and FIG. 21 is a partial, side view of the clamp applied to a vessel.

DETAILED DESCRIPTION OF PREFERRED EMBODIMENTS

Figures 1, 2:
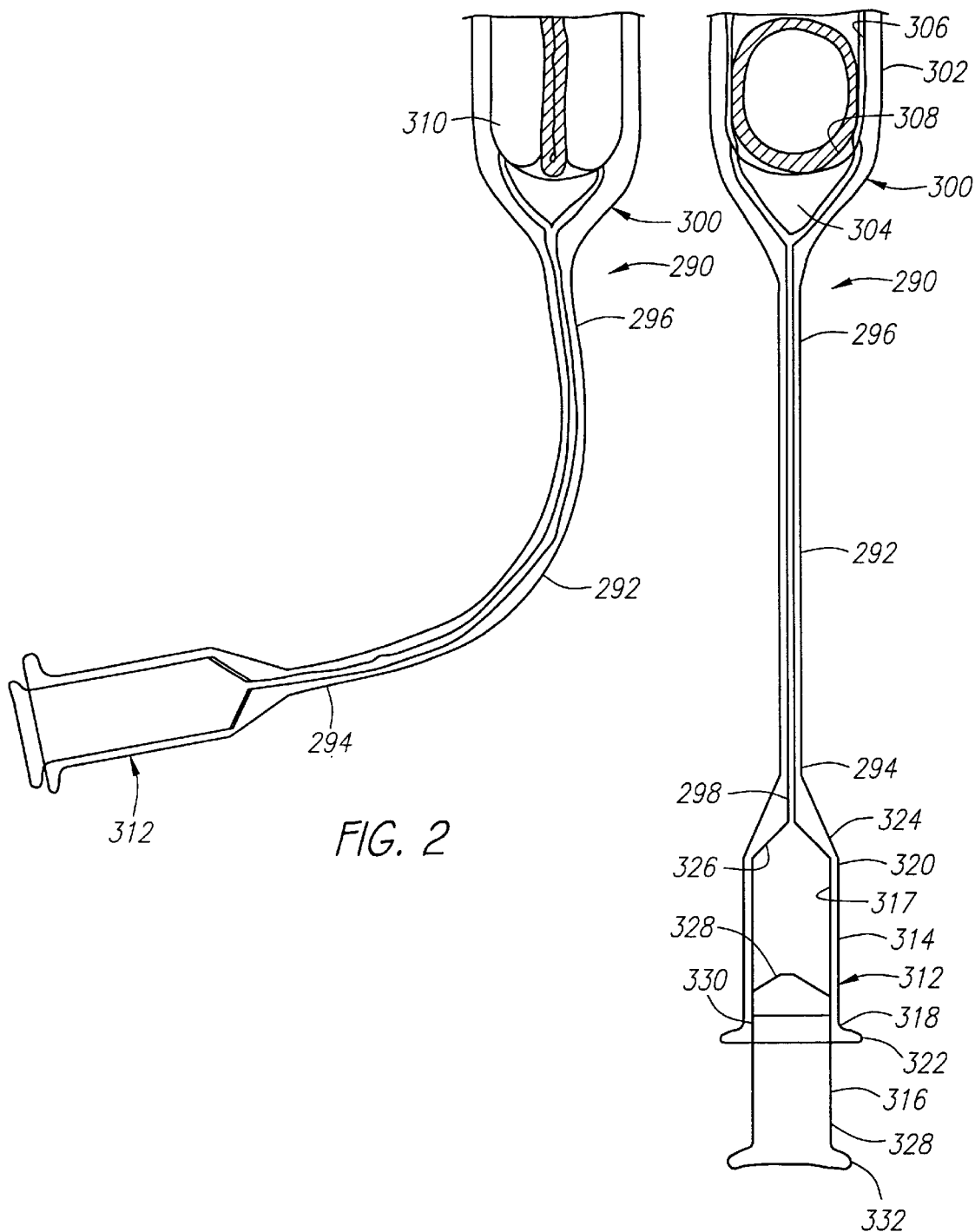
FIG. 1 is a top view of a vascular lamp constructed in accordance with an additional embodiment of the invention, and shows the clamp partially surrounding a vessel.
FIG. 2 is a top view of the vascular clamp of FIG. 1, and shows the clamp applied to a vessel and the handle in a bent-away position.

With reference to FIGS. 1–7 a vascular clamp, indicated generally by the reference numeral 290 and constructed in accordance with an embodiment of the invention, will now be described. The vascular clamp 290 includes an elongated shaft 292 which is preferably bendable with a proximal part 294 and distal part 296. The shaft 292 may be a braided or coiled shaft made of a physiologically acceptable metal or combination of metal and plastic. The shaft construction must be strong enough that it will not bend during insertion and application of the clamp 290, yet malleable enough that it can be bent out of the way of the surgical field without endangering the vessel. The shaft 292 includes at least one lumen 298 extending the longitudinal distance of the shaft 292.

Figure 7:
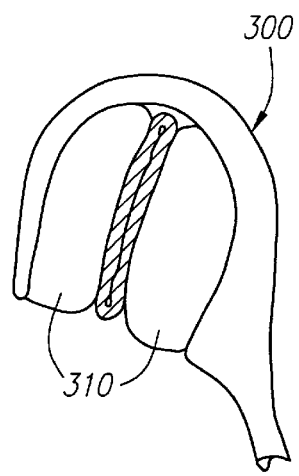
FIG. 7 is a partial, top view of a further embodiment of the frame; showing the balloon clamping members occluding a vessel.

With reference to FIGS. 1 and 7, the distal part 296 of the shaft 292 terminates in a generally U-shaped or C-shaped frame 300. The frame 300 includes a pair of prongs 302 joined at a junction 304. The prongs 302 and the junction 304 have respective inner wall sections, 306, 308. The prongs 302 are separated by a distance approximately equal to the diameter of the vessel or organ to be occluded. The frame 300 and the shaft 292 may carry fiber optics (not shown) for transferring light or other information along the thin glass fibers to assist in the cardiac procedure.

The balloons 310 can be made of one of the polyesters such as PET (polyethelene terephthatate) which is used in balloon angioplasty applications, one of the polyurethanes, a vinyl material or other similar less-elastic material. Even some of the very elastic materials such as latex, synthetic latex or silicone may be used if their final size is constrained physically by a web or mesh layer. A tubular mesh of less-elastic material, containing the balloon, and perhaps bonded to it, may also assist in attachment to prongs 302 as well as provide a grip-surface for the balloon/vessel interface. In any configuration, the balloons have a predetermined expanded size such that they do not expand beyond a set limit.

The balloons 310 have a high strength and collapse into a low profile. The balloons 310 have a generally circular or oblong cross-sectional shape; however, other balloon cross-sectional shapes may be used, such as, but not by way of limitation, rounded-triangular or ribbed. When viewing the balloon in a sagittal or side-view section, it follows the contour of prong 302, whether straight or curved.

Figure 3:
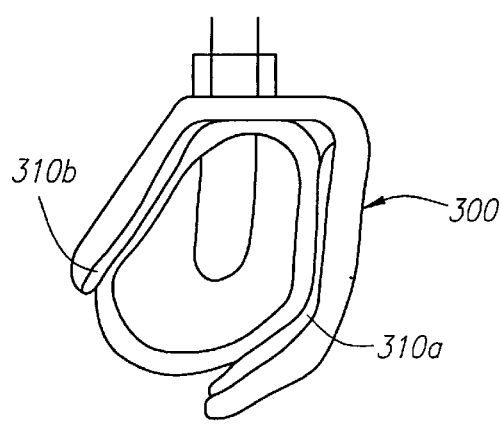
FIG. 3 is a partial, cross-sectional view of a vascular clamp frame constructed in accordance with an additional embodiment of the invention, and shows the balloon clamping members in a collapsed condition.
Figure 4:
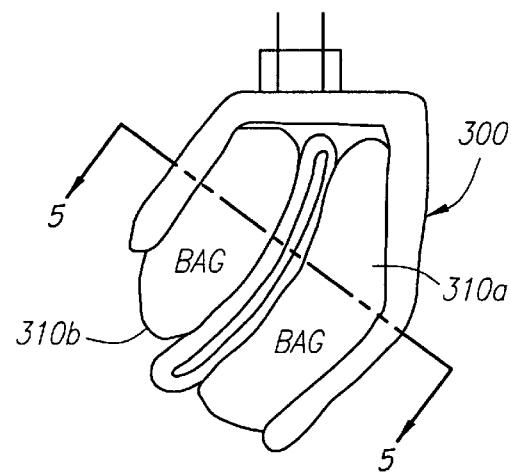
FIG. 4 is a view, similar to FIG. 3, and shows the balloon clamping members in a expanded condition.
Figure 5:
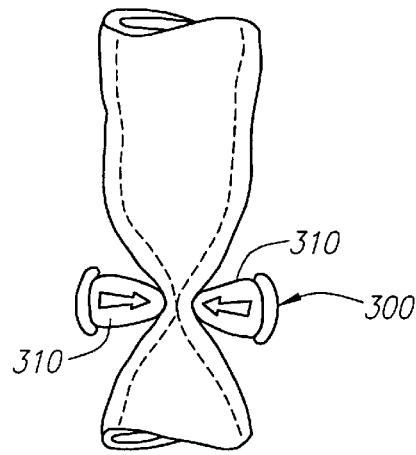
FIG. 5 is cross-sectional view taken along lines 11—11 of FIG. 4, and shows the balloon clamping members occluding a vessel.

It is important for the frame 300 to have a shape that allows the vascular clamp 290 to perform its intended purpose, i.e., occlude the vessel, without disturbing surrounding tissue. FIGS. 3–4 illustrate a frame 300 with a generally geometric configuration that is adapted for surrounding the aorta, for example, without disturbing surrounding tissue such as the tissue between the pulmonary artery and the aorta. In this embodiment, one balloon 310*a* is larger and has a slightly different shape than the other balloon 310*b*. Additionally, the larger balloon 310*a* is fixed to adjacent inner walls on one side of the frame 300 and the smaller balloon 310*b* is fixed to a single inner wall on the opposite side of the frame 300. FIG. 5 is a cross-sectional view of the clamp 290, taken along lines 11—11 of FIG. 4.

Figure 6:
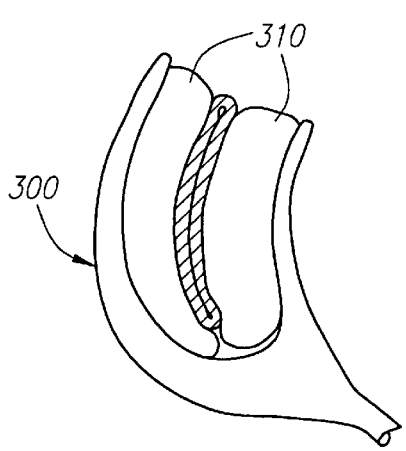
FIG. 6 is a partial, top view of another embodiment of the frame, showing the balloon clamping members occluding a vessel.

FIGS. 6 and 7 illustrate alternative frame embodiments. FIG. 6 shows a frame with a pair of curved prongs having different lengths. FIG. 7 shows a frame having a single prong which is more hook-shaped or sickle-shaped. Alternatively, similar to the shaft 292, the frame 300 may be made of a bendable material that may be molded to a predetermined shape that works ideally with a patient's individual tissue geometry. Similar to the shaft 292, the frame 300 must be strong enough that it will not bend during insertion of the clamp 290, application of the clamp 290 or inflation of the balloons 310, yet malleable enough that it can be deformed by the operator. They may be malleable only in the plane that is parallel to the long axis of the vessel and the clamp shaft. This would maintain the original distance between the prongs 302.

The balloons 310 are inflatable or expandable by means of a suitable medium such as air, water, or saline solution. The balloons 310 are in fluid communication with a fluid supply means via at least one lumen 298 (FIGS. 1 and 2). The at least one lumen 298 preferably comprises a single lumen that extends the length of the shaft 292 and forks at the junction 304 into a pair of lumens that communicating with a respective balloon 310. Alternatively, a pair of lumens may extend the length of the shaft 292 with each lumen communicating with a respective balloon 310. The proximal part 294 of the shaft 292 includes a fluid supply means, such as syringe mechanism 312 having a hollow barrel 314 and plunger 316. The hollow barrel 314 defines a chamber 317, and has a proximal end 318 and distal end 320. The chamber 317 is in fluid communication with the at least one lumen 298. The proximal end 318 includes a flange 322 and the distal end 320 includes a tapered portion 324 with a frustoconical interior 326. The plunger 316 includes a proximal end 328 and a distal end 330. The proximal end 328 includes a flange 332 and the distal end 330 includes a rubber seal 328. Pushing the plunger 316 causes a fluid such as water or saline to be injected into the balloons, expanding the balloons 310. Pulling the plunger 316 creating a negative pressure and causing the fluid to re-enter the chamber, collapsing the balloons 310.

Once the balloons 310 are expanded, positive pressure must be maintained within the balloons 310 so that the aorta remains occluded during the cardiac procedure. This may be accomplished in a number of ways, such as, but not by way of limitation, by providing a detent mechanism, which provides sufficient friction in the syringe mechanism 312 between the plunger 316 and the hollow barrel 314 so as to retain the plunger 316 in the inserted position, i.e. with the balloons 310 expanded, or by providing a one-way valve, e.g., check valve, that allows fluid to be injected into the balloons 310, but does not allow fluid to flow back into the chamber 317 unless the check valve is actuated. Because a one-way valve might not, in some circumstances, allow fluid to leave the balloon 310 quickly enough, the vascular clamp 290 may be configured to receive a vacuum tube or other device for immediately drawing fluid out of the balloons 310. Alternatively, a simple shut-off valve, manually operated and positioned at the distal end of syringe mechanism could effectively control the passage of fluid in lumen 298.

The vascular clamp 290 will now be described in use. If the vascular clamp 290 includes a bendable frame 300, the frame 300 may be deformed by the operator to a shape that is appropriate for occluding the patient's aorta while not disturbing surrounding tissue. The frame 300 is then applied partially around the aorta (FIGS. 1, 3). The plunger 316 is pushed into the chamber 317 of the hollow barrel 314, causing the fluid to be injected into the balloons 310 and expand the balloons 310. The balloons 310 serve as clamping members and compress the aorta upon expansion, occluding blood flow through aorta (FIGS. 2, 4, 5, 6, 7). The positive fluid pressure in the balloons 310 is maintained by the aforementioned detent mechanism friction between the plunger 316 and barrel 314, one-way valve, etc. Maintaining the positive fluid pressure in the balloons 310 effectively locks the balloons 310 on the aorta. The elongated shaft 292 is bent away from the surgical area of interest once the clamp 290 has been applied, reducing the obstructing effect of the clamp 290 on the surgery. If it becomes immediately necessary for the blood to flow through the occluded aorta, withdrawing the plunger 316 or disengaging the one-way valve causes fluid to flow back into the chamber 317, collapsing the balloons 310 so that the aorta is no longer occluded.

With reference to FIGS. 6–10, a vascular clamp, indicated generally by the reference number 340 and in accordance with a further embodiment of the invention, will now be described. The vascular clamp 340 includes a first elongated shaft 342 and second elongated shaft 344 that are in mating engagement and are slidable lengthwise relative to each other, and are preferably bendable or malleable. Each shaft 342, 344 has proximal and distal parts 346, 348, respectively.

With reference to FIG. 10, the first shaft 342 has an arcuate or generally C-shaped cross-section 350 that terminates in elongated ends 352, and an elongated inner surface 354. A lumen 356 extends the entire length of the shaft 342.

The second shaft 344 has an elongated main sliding portion 358 with a generally circular cross-section and an outer surface 360, a support rail 362 that extends radially from the main sliding portion 358. A lumen 364 extends through the center of the main sliding portion 358 the entire length of the shaft 344. The second shaft 344 slides on its outer surface 360 along the inner surface 354, within the generally C-shaped member 350. Although the distance between the ends 352 of the C-shaped member 350 is shown to be approximately the same as the width of the rail 362, in an alternative embodiment, the distance between the ends 352 may be larger, allowing rotation of the first shaft 342 relative to the second shaft 344.

Offset frame members 366, 368 are located at the distal parts 348 of the respective shafts 342, 344. Combined, the offset frame members 366, 368 form a frame 370. Similar to the frame 300 described above, the frame members 366, 368 may be deformable. An expandable/collapsible balloon 372 is fixed to an inner wall 374 of each frame member 366, 368. The balloons 372 are in fluid communication with the respective lumens 356, 364.

The proximal ends 346 of the respective shafts 342, 344 include slightly curved handles 376. Each handle 376 carries a squeezeable bladder 378 on one side of the handle 376 and a one-way valve 380 on the other side of the handle 376. The squeezeable bladder 378 includes a chamber (not shown) in fluid communication with the respective lumens 356, 364. The one-way valve 380 allows fluid, e.g., saline, air, etc., in the bladder 378 to be transferred to the balloon 372, expanding the balloon 372, and maintained in the balloon 372 until the one-way valve 380 is de-actuated, allowing the fluid to return to the chamber. Thus, the one-way valve 380 allows for the immediate collapsing of the balloons 372. If air is used as the fluid to expand the balloons 372, vents may be provided that allow air into the bladders 378 and out of the balloons 372. Because a one-way valve 380 or vent might not, in some circumstances, allow the fluid to leave the balloon 372 quickly enough, the vascular clamp 340 may be configured to receive a vacuum tube or other device that draws fluid out of the balloons 372.

Figure 13:
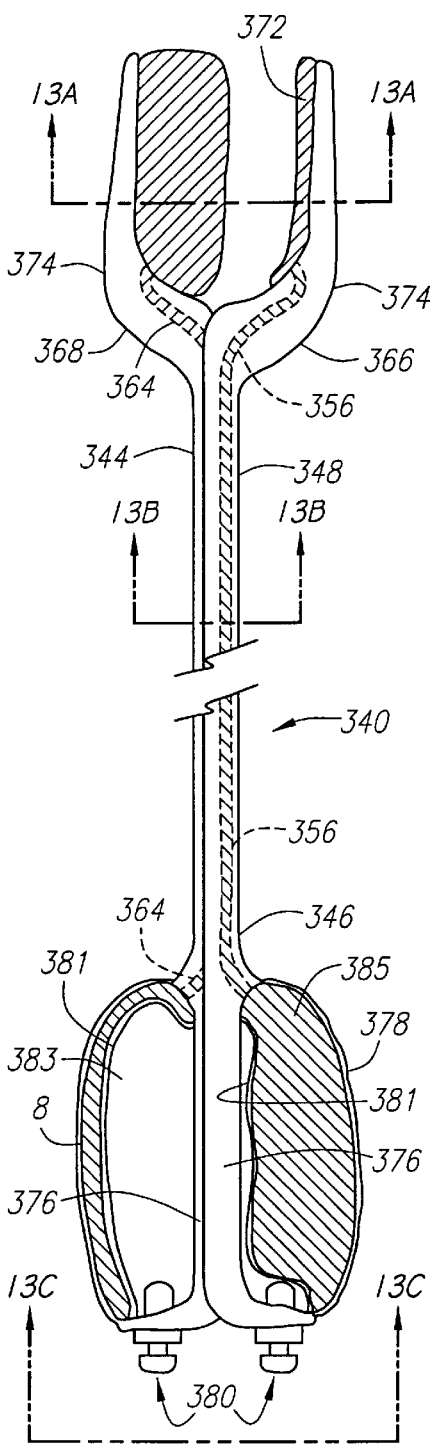
FIG. 13 is a top view of an additional embodiment of the present invention.
Figure 13A:
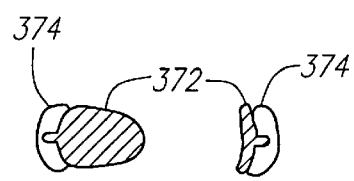
FIG. 13*a* is an end view cross-section taken along line A—A in FIG. 13.
Figure 13B:
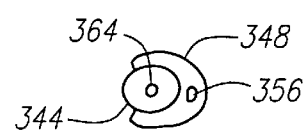
FIG. 13*b* is an end view cross-section taken along line B—B in FIG. 13.
Figure 13C:
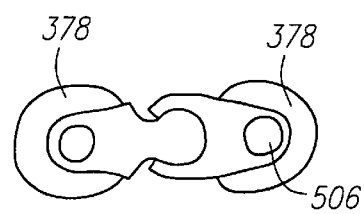
FIG. 13*c* is an end view cross-section taken along line C—C in FIG. 13.

With reference to FIGS. 13–14, an alternate embodiment of the present invention will be described. The vascular clamp 340 comprises a squeezeable bladder 378 comprised of two chambers, a first 383 in communication with the one-way valve 380 and a second 385 in communication with tubular lumen 356, for example. Separating the two lumens inside the bladder 378 is an elastic diaphragm 381 that allows either lumen to essentially occupy the entire interior space of bladder 378 at different times. There is, therefore, one continuous sealed volume that either fills a balloon 372 or a bladder 378 via the communicating tubular lumen 356 within the shaft 342, for example. This sealed volume is filled with the appropriate volume of liquid, i.e., saline, and initially occupies the second chamber, the squeezeable bladder 385.

Figures 14A, 14B:
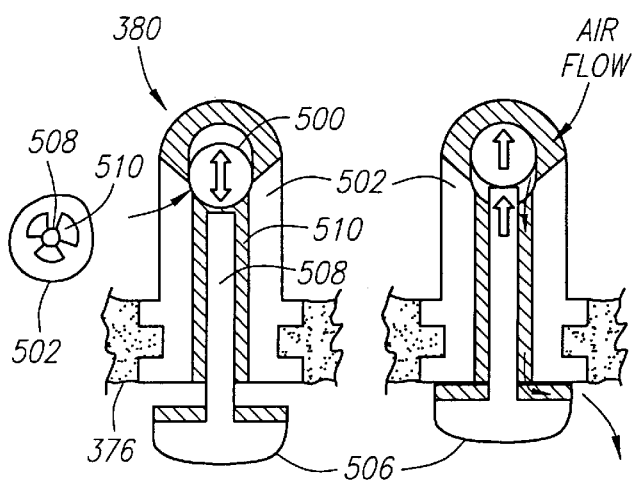
FIG. 14*a* and 14*b* is a detailed cut-away cross-section of the pressure relief valve for use with the present invention.

In use, at commencement of vessel occlusion, the squeezeable bladder 385 is manually pumped. Every squeeze forces fluid from the second bladder chamber into balloon 372, and every release draws air, being less viscous, into the first chamber 383 of bladder 378 through the valve 380. As can be seen in FIG. 14b, to deflate the balloon, the valve 380 can be either opened to allow air to escape or reversed in function to pump air out of the first chamber.

The advantageous reasons behind having an instrument with a sealed, fluid-filled operating chamber, filled with sterile saline solution, for example, that is pressurized with room air are twofold:

1) The part of the instrument that enters the body is filled with a fluid that will not injure the patient if ruptured, and, 2) The mechanical requirements of replacing the displaced volume of fluid upon inflation and vice versa, is simplified by using the inexhaustible supply of room air.

The vascular clamp 340 will now be described in use. As mentioned above, if the vascular clamp 340 includes a bendable frame 370, the frame 370 may be deformed by the operator to a desired shape that is appropriate for occluding the aorta of the particular patient while not disturbing surrounding tissue. The frame 370 is then applied partially around the aorta by introducing the offset frame member 368 and collapsed balloon 372 of one of the shafts 342, 344 to one side of the aorta (FIG. 11). This is done by sliding and rotating the shaft first applied 342, 344 relative to the other shaft 342, 344 so that the offset frame member 368, collapsed balloon 372 and shaft 342, 344 are maneuvered through the incision, around body tissue and to the side of the aorta. Because only half of the vascular clamp 340 has to be inserted and maneuvered at a time, the profile of the clamp 340 is very small. This makes the clamp 340 very suitable for manipulating the clamp 340 around body tissue and for minimally invasive surgery where the incision is small.

The second half of the clamp 340 is then slid into the mating half of clamp, the distal portion of the second half inserted into the proximal portion of the first half, and rotated into place on the opposite side of the aorta (FIG. 12). The balloons 372 are expanded by compressing the bladders 378. The balloons 372 serve as clamping members and compress the aorta upon expansion, occluding blood flow through aorta (FIGS. 9). The positive fluid pressure in the balloons 372 is maintained by the one-way valve 380. The elongated shafts 342, 344 are bent away from the surgical area of interest once the clamp 340 has been applied, reducing the obstructing effect of the clamp 340 on the surgery.

If it becomes immediately necessary for the blood to flow through the occluded aorta, actuating the one-way valve, vent, vacuum means, etc. causes fluid to flow out of each balloon 372, collapsing the balloons 372 which open the aorta.

Figure 15:
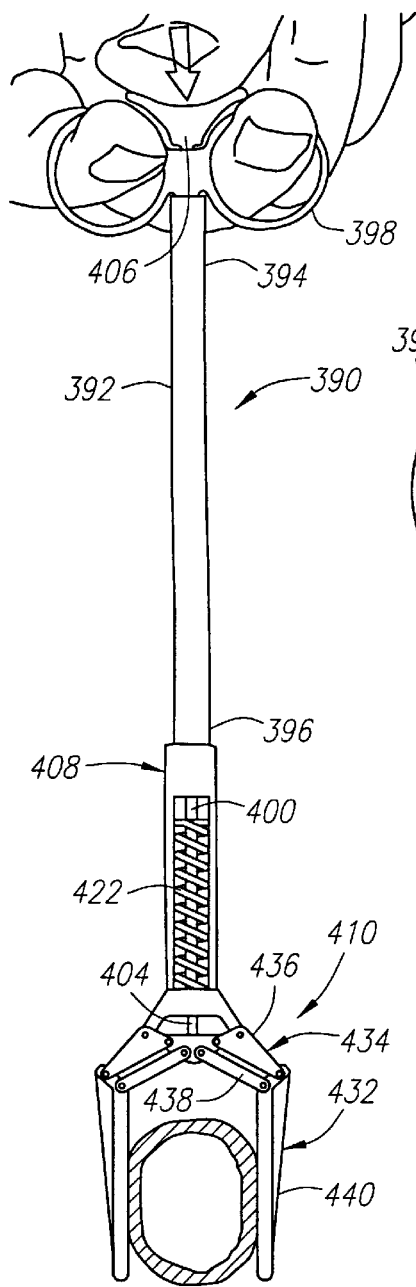
FIG. 15 is a top view of a further embodiment of the vascular clamp of the present invention, and shows the clamping members in an open position and partially surrounding a vessel.
Figure 16:
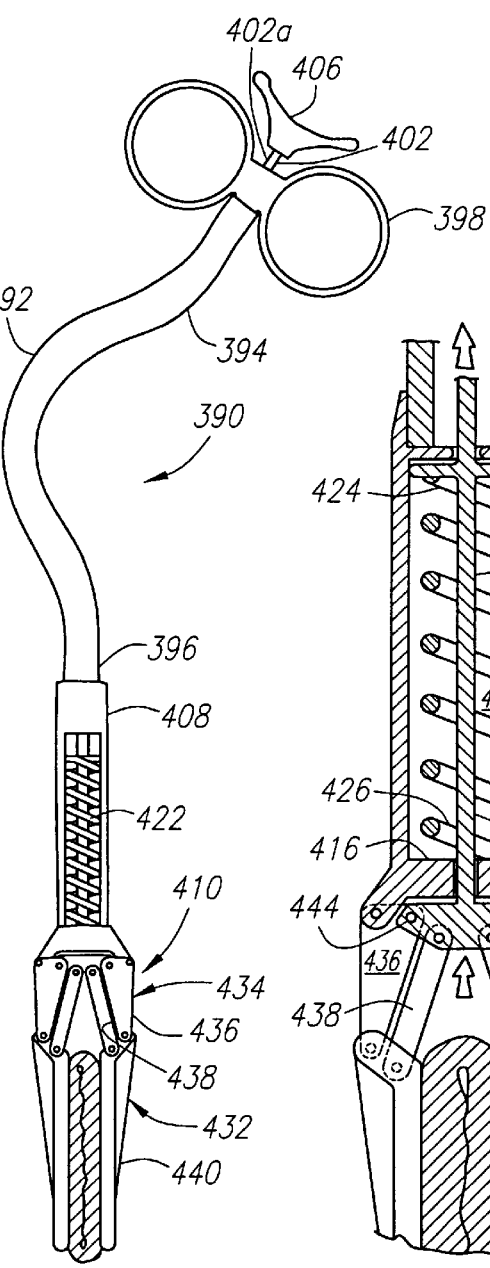
FIG. 16 is a top view, similar to FIG. 15, and shows the shaft and handle in a bent-away position and the clamp applied to the aorta.
Figure 17:
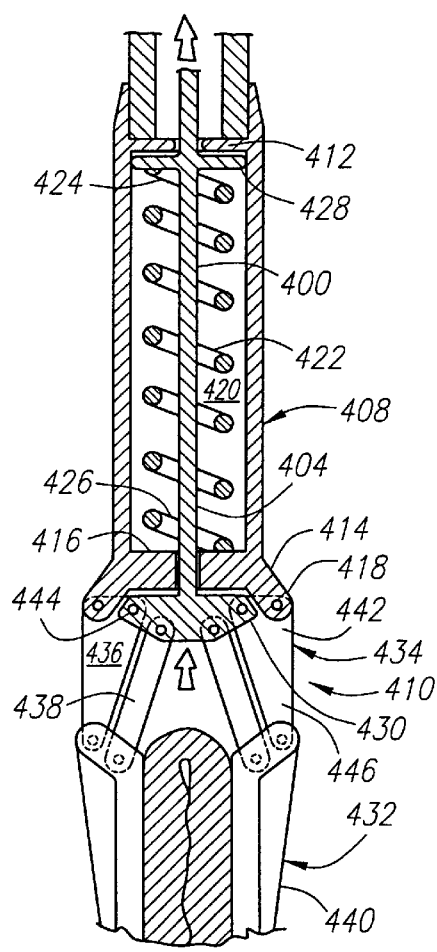
FIG. 17 is a partial, top view of a distal portion of the vascular clamp of FIG. 15.

With reference to FIGS. 15–17, a vascular clamp, indicated generally by the reference numeral 390 and in accordance with an additional embodiment, will now be described. The vascular clamp 390 includes a bendable shaft 392 with a proximal part 394 and a distal part 396. A handle 398 is fixed to the proximal part 394 of the shaft 392. A coaxial compression member 400, preferably a flexible cable with a proximal part 402 and a distal part 404 is carried by the shaft 392 and the handle 398. A plunger 406 adapted to fit a user's thumb is fixed to the proximal part 402 of the cable 400 by a short, inflexible, extendable shaft 402a.

The distal part 396 of the shaft 392 includes a generally tubular frame 408 with a clamping assembly 410 pivotally coupled thereto. With reference to FIG. 17, a proximal part of the frame 408 has a circular plate 412 with a hole for receiving the cable 400. A distal part of the frame 408 includes a trapezoidal base 414 with an upper face 416 and pair of extensions 418. An inner part of the frame 408 defines a cylindrical chamber 420 in which a compression spring 422 is disposed. The compression spring 422 has a predetermined compressive force so that the proper closing force is applied to the aorta by the clamp 390. The compression spring 422 includes a proximal end 424 and a distal end 426. The spring 422 is supported at its distal end 426 by the upper face 416. The proximal end 424 of the spring 422 abuts a circular flat plate 428 of the cable 400. The cable 400 terminates at its distal end in a trapezoidal member 430.

Instead of a cable arrangement, other means for transferring movement and forces from the plunger 406 to the trapezoidal member 430 may be used, such as, but not by way of limitation, a hydraulic arrangement.

The clamping assembly 410 includes a pair of clamping members 432 pivotally coupled to the extensions 418 and the trapezoidal member 430. Each clamping member 432 includes a pivoting portion, indicated generally by the reference numeral 434, comprising a first linkage 436 and a second linkage 438, and a clamping portion 440. The first linkage 436 is generally triangular in shape and is pivotally coupled at a proximal end to the extension 418 at an apex 442 and pivotally coupled to the trapezoidal member 430 at a first vertex 444. The second linkage 446 is pivotally coupled at a proximate end to the trapezoidal member 430. Together, the pivoting portions 434 form a four-bar linkage.

The clamping portion 440 is pivotally coupled to distal ends of the linkages 436, 438. The clamping portions 440 move generally parallel to each other within a generally longitudinal plane defined by the clamping portions 440.

The vascular clamp 390 will now be described in use. With reference to FIGS. 15 and 16, when the plunger 406 is not acted upon, clamping members 432 reside in a closed, clamped position. The clamping members 432 are maintained in this position by an upward, expanding force of the compression spring 422 against the circular flat plate 428, as shown by the arrows in FIG. 17. This upward force causes the trapezoidal member 430 to be maintained in an upper position, keeping the clamping portions 434 clamped together.

With reference to FIG. 15, downward movement of the cable 400 caused by an operator's thumb pressing or acting on the plunger 406 imparts downward movement to the trapezoidal member 430 if sufficient pressure is applied. This downward movement causes the clamping portions 434 to open. The clamp 390 is applied to or removed from the aorta with the clamping portions 440 open. When applying the clamp 390, the aorta is partially surrounded by the clamping portions 440, and the plunger 406 is released, causing the clamping portions 440 to compress the aorta with pressure sufficient to occlude blood flow through the aorta. The handle 398 is then bent out of the way from the surgical area of interest.

With reference to FIGS. 18–21, a vascular clamp, indicated generally by the reference numeral 450, and constructed in accordance with an additional embodiment of the invention, will now be described. The vascular clamp 450 includes a bendable shaft 452 with a proximal part 454 and a distal part 456. A handle 458 is fixed to the proximal part 454 of the shaft 452. A coaxial compression cable 460 with a proximal part 462 and a distal part 464 is carried by the shaft 452 and the handle 458. A plunger 466 adapted to fit a user's thumb is fixed to the proximal part 462 of the cable 460. The distal part 456 of the shaft 452 includes a generally tubular guide frame 467 that guides the cable 460, particularly the otherwise unsupported distal part 464, and a clamping assembly 468.

With reference to FIG. 18, the clamping assembly 468 has a generally V-shaped configuration and includes a pair of elongated, slightly curved clamping members 470. The clamping members 470 include respective elongated cut-outs 472 and are joined at a pair of vertices 474, which are fixed to opposite sides of the distal part 456 of the shaft 452. Each cut-out 472 terminates at a distal end near a pin 476. The pin 476 is used to pivotally couple a distal end of a respective linkage 478 to the clamping member 470. The linkages 478 are pivotally coupled at a proximal end to the distal part 474 of the cable 460. A tension spring 480 coaxially surrounds the distal part 464 of the cable 460 and is connected at a proximal end to the frame 467. The distal part of cable 464 is a rigid shaft, as it transmits compressive force without the support of a cable housing. The tension spring 480 has a predetermined tension that imparts the proper amount of compression on the aorta.

The vascular clamp 450 will now be described in use. With reference to FIGS. 20, the clamping members 470 reside in a normally closed, clamped position caused by the tension spring 480 pulling on the proximal ends of the linkages 478. The pulling of the spring 480 causes the clamping members 470 to be maintained together.

With reference to FIGS. 18 and 19, pressing or acting upon the plunger 466 with sufficient pressure causes the cable 460 to impart movement to the proximal ends of the linkages 478, opening the clamping members 470. The clamp 450 is applied to, or removed from, the aorta with the clamping members 470 open. When applying the clamp 450, the aorta is partially surrounded by the clamping members 470, and the plunger 466 is released, causing the clamping members 470 to compress the aorta with pressure sufficient to occlude blood flow through the aorta. The handle 458 is then bent out of the way from the surgical area of interest to inhibit obstruction with the cardiac procedure.

It will be readily understood by those skilled in the art, that certain components, aspects, principles, etc., of any of the above-described embodiments, may be applied to other embodiments, such as, but not by way of limitation, the clamp materials, the locking means, the quick release mechanism, the clamping assembly, and the manner in which the size, shape, and configuration of clamping members are moved. Although this invention has been described in terms of a preferred embodiments, other embodiments apparent to those of ordinary skill in the art are also within the scope of this invention. Accordingly, the scope of this invention is intended to be defined only by the claims that follow.

What is claimed is:

1. A surgical clamp suitable for temporarily occluding a vessel during surgery, comprising:

at least one bendable elongated shaft, said at least one bendable elongated shaft comprising a pair of elongated, bendable shafts and having a proximal part and a distal part, said pair of elongated, bendable shafts being slidable lengthwise relative to each other;

a pair of clamping members located at the distal part of the shaft; and means for moving the clamping members apart from each other to an open position for surrounding a portion of the blood vessel and towards each other to a clamping position for compressing the blood vessel with pressure sufficient to occlude blood flow through the blood vessel, whereby said elongated shaft is capable of being bent away from the surgical area of interest, reducing the obstructing effect of the surgical clamp on the surgery.

2. The surgical clamp of claim 1, further including a spring that imparts a closing force on the clamping members.

3. A surgical clamp suitable for temporarily occluding a vessel during surgery, comprising:

at least one bendable elongated shaft, said at least one bendable elongated shaft having a proximal part, a distal part, and at least one lumen;

a pair of clamping members located at the distal part, of the shaft, said pair of clamping members each comprising at least one inflatable balloon, said at least one inflatable balloon being in fluid communication with said at least on lumen of said at least one bendable elongated shaft; and means for moving the clamping members apart from each other to an open position for surrounding a portion of the blood vessel and towards each other to a clamping position for compressing the blood vessel with pressure sufficient to occlude blood flow through the blood vessel, whereby said elongated shaft is capable of being bent away from the surgical area of interest, reducing the obstructing effect of the surgical clamp on the surgery.

4. The surgical clamp of claim 3, wherein said shafts are rotatable relative to each other.

5. The surgical clamp of claim 3, wherein each shaft includes a bladder fixed at the proximal part and a balloon at the distal part, a lumen is carried by the elongated shaft and communicates the bladder with the balloon, a first shaft has a generally arcuate cross section and an elongated inner surface, a second shaft has a cross section having a configuration for mating engagement with the first shaft and an outer surface, and the second shaft is slidably received within said other shaft and its outer surface is slidably engaged with the inner surface of the first shaft.

6. The surgical clamp of claim 3 wherein the cross-section of the first shaft is C-shaped and the cross-section of the second shaft is generally circular.

7. The surgical clamp of claim 3, further including a spring that imparts a closing force on the clamping members.

8. The surgical clamp of claim 3, further including at least one compressible bladder that is in fluid communication with said at least one lumen for imparting positive fluid pressure to said balloons for expanding the balloons.

9. The surgical clamp of claim 8, further including a one-way valve that is carried by one of the shafts adjacent to the proximal part of the shafts, and the one way valve adapted to immediately reduce the fluid pressure in said balloons.

10. The surgical clamp of claim 8, wherein said at least one shaft includes a single, elongated shaft, a handle located at the proximal part of the shaft, and an actuator is located at the proximal part of the shaft for imparting opening movement to the clamping members.

11. The surgical clamp of claim 8, wherein said clamping members include a four bar linkage that is operatively associated with a pair of clamping portions, the spring includes a compression spring that imparts a constant closing force on said clamping portions, said actuator includes a plunger and a coaxial cable that is coupled at a proximal part to the plunger and at a distal part to the clamping members, and whereby pushing said plunger with sufficient pressure imparts opening movement to said clamping members.

12. The surgical clamp of claim 8, wherein said clamping members include respective elongated clamping portions, the spring includes a tension spring that imparts a constant closing force on said clamping portions, said actuator includes a plunger and a coaxial cable coupled at a proximal part to the plunger and at a distal part to the clamping members, and whereby pushing said plunger with sufficient pressure imparts opening movement on said clamping members.

13. A method of temporarily occluding a blood vessel during surgery, comprising the steps of:

providing a vascular clamp comprising at least one bendable elongated shaft with a proximal part and distal part, a pair of clamping members located at the distal part of the shaft, and means for moving the clamping members apart from each other to an open position and towards each other to a clamping position;

clamping the blood vessel by compressing the blood vessel with the clamping members with pressure sufficient to occlude blood flow through the section;

bending the elongated shaft away from the surgical area of interest, reducing the obstructing effect of the vascular clamp on the surgery;

providing first and second elongated shafts, said first and second elongated shafts being slidable lengthwise relative to each other and rotatable relative to each other, said first and second elongated shafts each having a balloon located at a distal part of said shaft and a bladder located at a proximal part of said shaft, said balloon and said bladder being in fluid communication with each other through a lumen; and applying the clamp to the blood vessel by manipulating one of the shafts by sliding and rotating it relative to the other shaft and by manipulating the other shaft by sliding and rotating it relative to the first shaft.

14. A method of temporarily occluding a blood vessel during surgery, comprising the steps of:

providing a vascular clamp comprising at least one bendable elongated shaft with a proximal part and distal part, a pair of clamping members located at the distal part of the shaft, and means for moving the clamping members apart from each other to an open position and towards each other to a clamping position;

clamping the blood vessel by comprising the blood vessel with the clamping members with pressure sufficient to occlude blood flow through the section;

bending the elongated shaft away from the surgical area of interest, reducing the obstructing effect of the vascular clamp on the surgery;

providing a spring, said spring being carried by said at least one shaft and imparting a closing force on the clamping members, an actuator being carried by the proximal part of the shaft for imparting opening movement to said clamping members;

opening said clamping members by acting upon said actuator with sufficient pressure; and relieving pressure on said actuator so that said spring imparts closing movement to the clamping members compressing the blood vessel.

\* \* \* \* \*

UNITED STATES PATENT AND TRADEMARK OFFICE
CERTIFICATE OF CORRECTION

PATENT NO. : 6,146,394

DATED : November 14, 2000

INVENTOR(S) : Dwight P. Morejohn et al.

It is certified that error appears in the above-identified patent and that said Letters Patent is hereby corrected as shown below:

Column 11, line 62, remove the comma after the term 'distal part';

Column 14, line 5, remove the word 'comprising' and replace with --compressing--.

Column 14, line 20, insert --for-- after 'members'.

Signed and Sealed this

Twenty-ninth Day of May, 2001

Attest:

NICHOLAS P. GODICI

Attesting Officer      Acting Director of the United States Patent and Trademark Office